(12) United States Patent
Wang et al.

(10) Patent No.: US 11,029,279 B2
(45) Date of Patent: Jun. 8, 2021

(54) METHOD OF DETECTING CELLS

(71) Applicant: National Tsing Hua University, Hsinchu (TW)

(72) Inventors: Yu-Lin Wang, Hsinchu (TW); Anil Kumar Pulikkathodi, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 540 days.

(21) Appl. No.: 15/989,204

(22) Filed: May 25, 2018

(65) Prior Publication Data

US 2019/0346402 A1 Nov. 14, 2019

(30) Foreign Application Priority Data

May 9, 2018 (TW) .............................. 107115775.0

(51) Int. Cl.
*G01N 27/414* (2006.01)
*G01N 33/543* (2006.01)

(52) U.S. Cl.
CPC ..... *G01N 27/4145* (2013.01); *G01N 27/4146* (2013.01); *G01N 33/5438* (2013.01)

(58) Field of Classification Search
CPC ........... G01N 33/5438; G01N 27/4145; G01N 27/4146; G01N 33/56966
See application file for complete search history.

(56) References Cited

U.S. PATENT DOCUMENTS

| 9,389,199 | B2 | 7/2016 | Cheng et al. | |
|---|---|---|---|---|
| 2015/0087552 | A1* | 3/2015 | Jensen | .......... C12Q 1/42 506/10 |
| 2016/0282295 | A1 | 9/2016 | Wang et al. | |
| 2016/0305900 | A1 | 10/2016 | Wang et al. | |
| 2017/0016916 | A1* | 1/2017 | Wang | ............ G01N 33/6893 |

FOREIGN PATENT DOCUMENTS

| CN | 1504578 | 6/2004 |
|---|---|---|
| CN | 102803944 | 11/2012 |
| CN | 103913489 | 7/2014 |

(Continued)

OTHER PUBLICATIONS

Pulikkathodi et al., "Aptamer Functionalized AlGaN/GaN HEMT Biosensor Array for Electrical Enumeration of Circulating Tumor Cells", ECS Trans., May 25, 2017, pp. 1-4.

(Continued)

*Primary Examiner* — Robert G Bachner
(74) *Attorney, Agent, or Firm* — JCIPRNET (57) ABSTRACT

A method of detecting cells is provided. The method includes the following steps. A sensor device including a base and at least one response electrode is provided, wherein the response electrode is spaced apart from the base with respect to a gate end of the base. A test solution containing a target cell is placed on the response electrode, a first pulse voltage is applied to the response electrode, and a first detection current generated from the base is measured. A membrane potential of the target cell is changed, a second pulse voltage is applied to the response electrode, and a second detection current generated from the base is measured, wherein a sign of the first detection current and a sign of the second detection current are opposite.

10 Claims, 5 Drawing Sheets

(56) References Cited

FOREIGN PATENT DOCUMENTS

| CN | 104303056 | 1/2015 |
|---|---|---|
| CN | 104303050 | 3/2018 |

OTHER PUBLICATIONS

Pulikkathodi et al., "Dynamic monitoring of transmembrane potential changes: a study of ion channels using an electrical double layer-gated FET biosensor", Lab Chip, Mar. 27, 2018, pp. 1047-1056.

Pulikkathodi et al., "A Comprehensive Model for Whole Cell Sensing and Transmembrane Potential Measurement Using FET Biosensors", ECS Journal of Solid State Science and Technology, Feb. 7, 2018, pp. Q3001-Q3008.

Pulikkathodi et al., "Enumeration of circulating tumor cells and investigation of cellular responses using aptamer-immobilized AlGaN/GaN high electron mobility transistor sensor array", Sensors and Actuators, Oct. 28, 2017, pp.96-104.

"Office Action of Taiwan Counterpart Application," dated Jan. 18, 2019, p. 1-p. 3.

\* cited by examiner

METHOD OF DETECTING CELLS

CROSS-REFERENCE TO RELATED APPLICATION

This application claims the priority benefit of Taiwan application serial no. 107115775, filed on May 9, 2018. The entirety of the above-mentioned patent application is hereby incorporated by reference herein and made a part of this specification.

BACKGROUND OF THE INVENTION

Field of the Invention

The invention relates to a method of detecting a biological sample, and more particularly, to a method of detecting cells.

Description of Related Art

Circulating tumor cells (CTC) are migrating cells in the body circulation system, and are clinically-important cancer biomarkers that can be used in the detection of early-stage cancer and the metastasis of cancer cells.

CTCs are very rare in blood (1 to 10 CTCs/1 mL), and therefore the detection of CTCs is rather difficult. Positive selection can currently be performed using immunomagnetic separation, immunofluorescence, and a flow cytometric technique. However, immunomagnetic separation and immunofluorescence have the issue of lacking receptor specificity, and the sensitivity of the flow cytometric technique relies on a large amount of sample. Therefore, how to develop a method of detecting CTCs having high sensitivity, high accuracy, and low detection limit is an urgent topic for those skilled in the art.

SUMMARY OF THE INVENTION

The invention provides a method of detecting cells having the properties of high sensitivity, high accuracy, and low detection limit.

The invention provides a method of detecting cells including the following steps. A sensor device is provided, wherein the sensor device includes a base and at least one response electrode, and the response electrode is spaced apart from the base with respect to a gate end of the base. A test solution containing a target cell is placed on the response electrode, and a first pulse voltage is applied to the response electrode to generate a first electric field between the response electrode and the gate end of the base, and a first detection current generated by the base is measured. A membrane potential of the target cell is changed, a second pulse voltage is applied to the response electrode to generate a second electric field between the response electrode and the gate end of the base, and a second detection current generated by the base is measured, wherein a sign of the first detection current and a sign of the second detection current are opposite.

According to an embodiment of the invention, the first electric field and the second electric field are F, and $0.1 \text{ V/cm} \leq F \leq 10 \text{ V/cm}$.

According to an embodiment of the invention, the sensor device can further include an acceptor disposed on a surface of the response electrode, wherein the acceptor can be specifically bonded to the target cell.

According to an embodiment of the invention, the acceptor is, for instance, an antibody or an aptamer.

According to an embodiment of the invention, the first detection step includes the following.

A first current gain generated by the base is measured and a second current gain generated by the base is measured, wherein the first current gain is a current gain before the test solution is placed, the second current gain is a current gain after the test solution is placed, and the first detection current is the second current gain minus the first current gain.

According to an embodiment of the invention, the second detection step includes the following.

A third current gain generated by the base is measured and a fourth current gain generated by the base is measured, wherein the third current gain is a current gain before the test solution is placed, the fourth current gain is a current gain after the membrane potential of the target cell is changed, and the second detection current is the fourth current gain minus the third current gain.

According to an embodiment of the invention, a method of changing the membrane potential of the target cell includes, for instance, applying an external stimulus to the target cell.

According to an embodiment of the invention, the external stimulus includes, for instance, a change in ion concentration, a chemical signal molecule, a light, or a sound wave.

According to an embodiment of the invention, the first pulse voltage and the second pulse voltage are, for instance, pulse voltages having adjustable pulse width and height.

According to an embodiment of the invention, the pulse width can be not greater than $10^{-3}$ seconds.

According to an embodiment of the invention, the response electrode and the gate end of the base can be located on the same plane.

Based on the above, in the method of detecting cells of the invention, by changing the membrane potential of the target cells to detect a change in the current gain in order to determine the presence of the target cells, the method has the properties of high sensitivity, high accuracy, and low detection limit.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
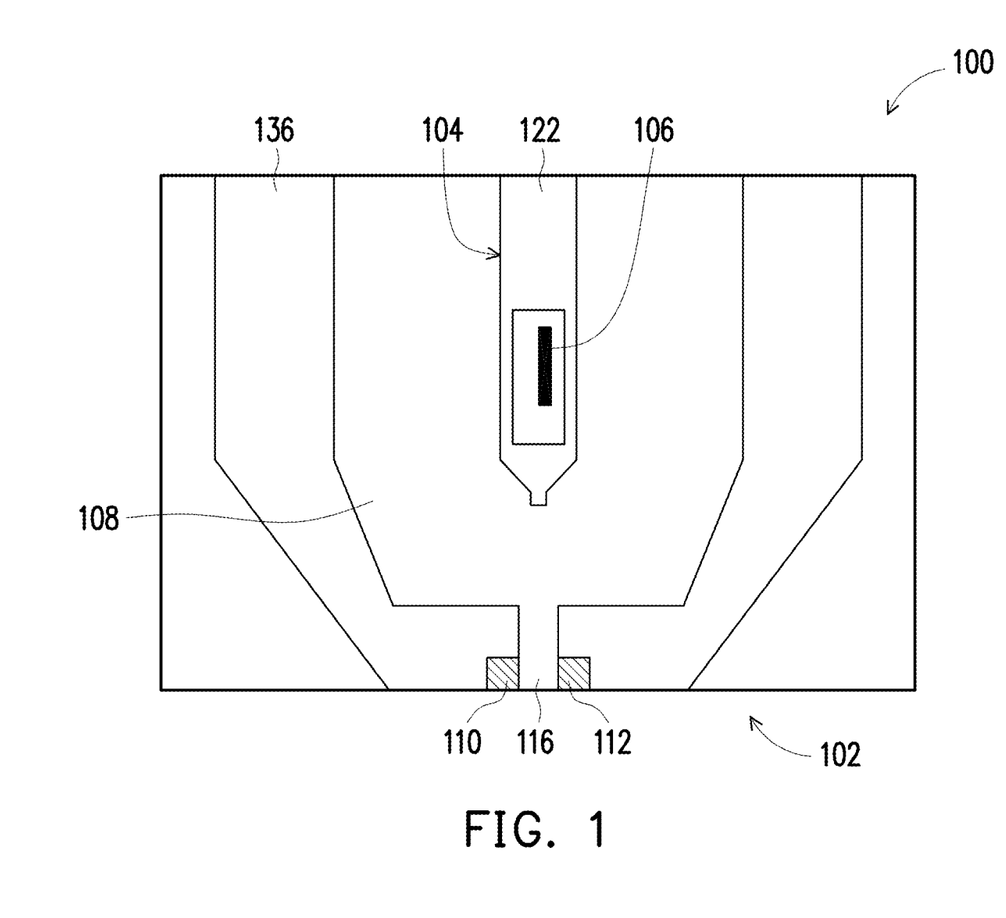
FIG. 1 is a top view of a sensor device according to an embodiment of the invention.

FIG. 1 is a schematic of a sensor device according to an embodiment of the invention.

Referring to FIG. 1, a sensor device 100 includes a base 102 and a response electrode 104, wherein the response electrode 104 and the base 102 are spaced apart from each other. The sensor device 100 is, for instance, a high electron mobility transistor (HEMT), a silicon-based field-effect transistor, a nanowire field-effect transistor, a carbon nanotube field-effect transistor, a graphene field-effect transistor, or a molybdenum disulfide field-effect transistor, but the invention is not limited thereto. In the present embodiment, the sensor device 100 is a transistor similar to a high electron mobility transistor.

The base 102 includes a substrate 108, a source end 110, a drain end 112, and a gate end 116 disposed between the source end 110 and the drain end 112. In the present embodiment, the method of forming the substrate 102 includes, for instance, forming a gallium nitride (GaN) layer and an aluminum gallium nitride (AlGaN) layer (not shown) on the substrate 108 in order and forming the source end 110, the drain end 112, and the gate end 116 on the substrate 108 via a lithography process.

The material of the substrate 108 is, for instance, silicon, sapphire, or a combination thereof. The low-dimensional heterostructure interface between the GaN layer and an aluminum gallium nitride layer (not shown) can provide the base 102 with good carrier transport properties. In the present embodiment, the material formed on the GaN layer is aluminum indium nitride, but the invention is not limited thereto. In another embodiment, the material formed on the GaN layer can be other materials having piezoelectric properties, such as aluminum gallium nitride. The material of the source end 110 and the drain end 112 can include one or more than one conductive material. The conductive material is, for instance, a metal material, metal compound, or a combination thereof. The source end 110 and the drain end 112 are respectively connected to an external electronic device (not shown) via a circuit 136.

Referring further to FIG. 1, the response electrode 104 is disposed on the substrate 102. The response electrode 104 includes an electrode body 122 located on the top surface of the base 102, and the electrode body 122 is formed by a metal material. The response electrode 104 can be located on the same plane as the gate end 116 and the two can be spaced apart and disposed opposite to each other. More specifically, the electrode body 122 can be located on the same plane as the gate end 116 of the base 102 and the two can be spaced apart from each other and disposed opposite to each other, and the electrode body 122 and the base 102 are not electrically connected. Specifically, the electrode body 122 and the gate end 116 are not electrically connected. It should be mentioned that, the surface material of the electrode body 122 is selected from materials that can be bonded to a subsequently-selected acceptor 106. In the present embodiment, the surface material of the electrode body 122 is, for instance, gold.

Figure 2:
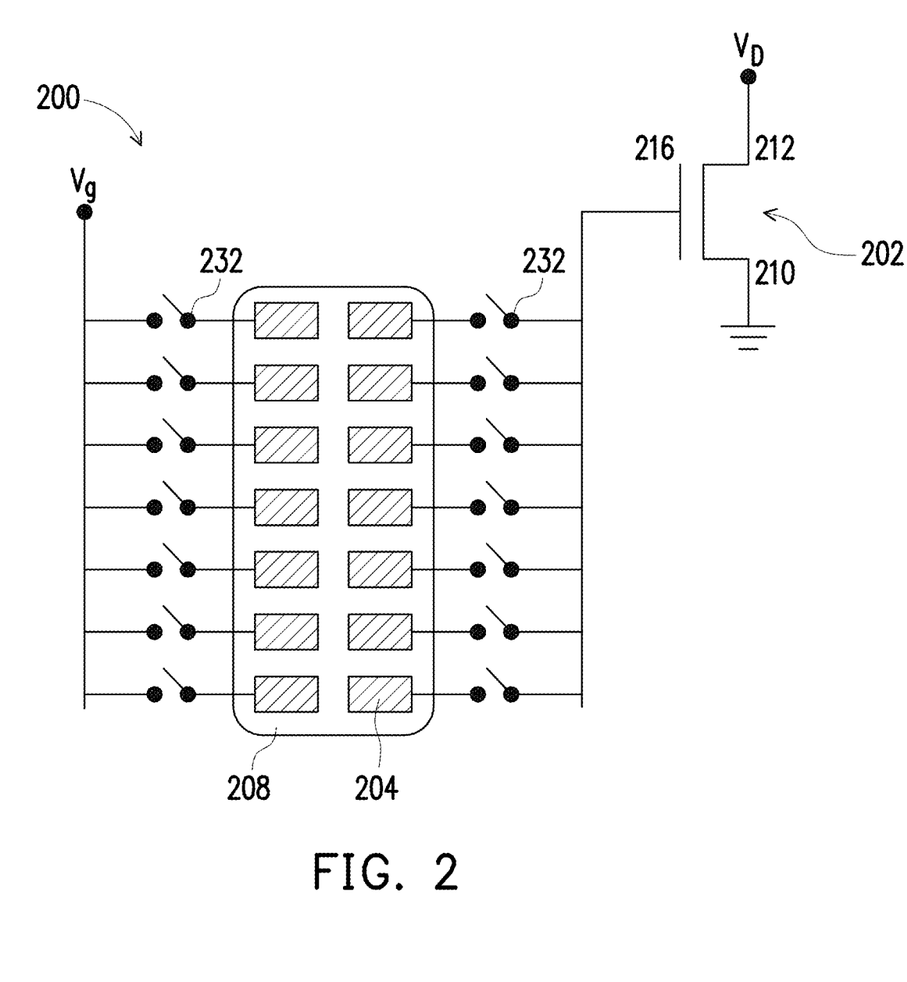
FIG. 2 is a top view of a sensor device according to another embodiment of the invention.

FIG. 2 is a top view of a sensor device according to another embodiment of the invention. A sensor device 200 shown in FIG. 2 is similar to the sensor device 100 shown in FIG. 1, and the difference is that the sensor device 200 has a plurality of response electrodes 204, and the plurality of response electrodes 204 are spaced apart from one another on the substrate 208 to form a detection region (not shown), and the same or similar components are described in detail above and are not repeated herein.

Referring to FIG. 2, the sensor device 200 includes a plurality of response electrodes 204, and the plurality of response electrodes 204 correspond to a same base 202. As a result, the sensor device 200 can perform a plurality of tests on a test solution at the same time, which not only can increase the reliability of the test result, but can also reduce the time needed for the test. Moreover, since a plurality of response electrodes 204 share the same base 202 and only the used response electrodes 204 need to be replaced to perform the next test, the cost for the test can be reduced.

In an embodiment, the sensor device 200 further includes a plurality of switch circuits 232 and each of the response electrodes 204 is connected to the corresponding switch circuit 232 to selectively control the desired response electrode 204, such that the sensor device 200 is suitable for various measurement methods, such as testing the same test solution at different times to observe the amount of change of concentration and time. In some embodiments, the switch circuits 232 are located at two opposite sides of the response electrode 204. The switch circuit 232 located at a side of the response electrode 204 is connected to a gate voltage $V_g$ (pulse voltage applied to the response electrode), and the switch circuit 232 located at another side of the response electrode 204 is connected to the gate end 216. Moreover, during the measurement, the source end 210 of the base 210 is grounded and a drain voltage $V_D$ is applied to the drain end 212.

The invention also provides a method of detecting cells using the sensor device above. In an embodiment of the invention, the method of detecting cells includes: a preparation step, a first detection step, and a second detection step. Next, the method of detecting cells of the invention is described via the sensor device 100 shown in FIG. 1.

First, the preparation step is performed: a sensor device 100 is provided, wherein the sensor device 100 includes a base 102 and at least one response electrode 104, and the response electrode 104 is spaced apart from the base 102 with respect to the gate end 116 of the base 102. In the present embodiment, the acceptor 106 can be bonded to the surface of the electrode body 122, wherein the acceptor 106 can be bonded to the target cells in a subsequent test solution to be tested. The acceptor 106 is, for instance, an antibody or an aptamer.

Next, the first detection step is executed: the test solution containing the a target cell is placed on the response electrode 104, and a first pulse voltage V1 is applied to the response electrode 104 to generate a first electric field F1 between the response electrode 104 and the gate end 116 of the base 102, and a first detection current generated by the base 102 is measured.

In an embodiment, the test solution is, for instance, a whole blood containing the target cells. In another embodiment, the test solution is, for instance, a test solution containing the target cells and a buffer solution (or cell culture medium). The buffer solution is, for instance, phosphate buffer saline (PBS) or a Hanks balanced salt solution (HBSS), but the invention is not limited thereto. The medium is, for instance, an RPMI-1640 cell culture medium. In an embodiment, the target cells are, for instance, tumor cells or cancer cells, but the invention is not limited thereto. In the present embodiment, the test solution is directly in contact with the acceptor 106 on the response electrode 104, and the target cells in the test solution are specifically bonded to the acceptor 106 on a surface of the response electrode 104.

In an embodiment, the target cells are human colorectal cancer cell line HCT-8 cells, and the acceptor is an aptamer that can be specifically bonded to the HCT-8 cells.

In the present embodiment, since the acceptor 106 on the surface of the response electrode 104 is directly and specifically in contact with the target cells, interference from other cells can be avoided during the process of detecting the target cells, such that a more precise detection result can be obtained.

Specifically, the first detection step includes first providing a fixed voltage to the base 102 and then applying a first pulse voltage V1 to the response electrode 104 to generate a voltage difference between the response electrode 104 and the gate end 116. Therefore, when the target cells of the test solution are specifically bonded to the acceptor, a capacitance effect occurs between the response electrode 104 and the gate end 116 via the voltage difference generated by the application of the first pulse voltage V1 to obtain a detection current value contributed by the capacitance effect. The target cells bonded to the acceptor are detected according to the detection current value. It should be mentioned that, when detection is performed using the capacitance effect, dynamic information of the bonding between the acceptor and the target cells before the reaction reaches a balanced state can be measured. In other words, by measuring the dynamic information before the reaction reaches a balanced state, the known shielding effect generated when human blood is balanced by high salt concentration as a result of measuring at a balanced state can be overcome, and a complex dilution step is also not needed for the human blood.

In the present embodiment, the first pulse voltage V1 is a pulse voltage having adjustable pulse width and height. The size of the pulse width and the height of the first pulse voltage V1 can be adjusted according to the test duration for the analysis and the size of the voltage needed for the test. In an embodiment, a time before the bonding reaction between the acceptor and the target cells reaches a balance is used for the pulse width, and the pulse width is not greater than $10^{-3}$ seconds, but the invention is not limited thereto. In an actual example, the pulse height is, for instance, 0.5 V, but the invention is not limited thereto.

In an embodiment, the first electric field F1 is between 0.1 V/cm and 10 V/cm (0.1 V/cm≤F1≤110 V/cm). In another embodiment, the first electric field F1 is between 0.5 V/cm and 10 V/cm (0.5 V/cm≤F1≤1.0 V/cm). In yet another embodiment, the first electric field F1 is between 0.5 V/cm and 1.0 V/cm (0.5 V/cm≤F1≤1.0 V/cm). The applied electric field F1 can have low detection limit and high sensitivity within the ranges above.

In the present embodiment, the first detection step can include the following sub-steps: a first current gain generated by the base is measured and a second current gain generated by the base is measured, wherein the first current gain is a current gain before the test solution is placed, the second current gain is a current gain after the test solution is placed, and the first detection current (i.e., change in current gain) is the second current gain minus the first current gain.

In the present embodiment, the current gain represents the difference between a balance current value and an initial current value (i.e., background current) (i.e., balance current value-initial current value=current gain). The initial current value can represent a current value obtained by applying an initial voltage to the response electrode. In the present embodiment, the initial voltage can be less than the gate voltage, but the invention is not limited thereto. The balance current value can represent a current value obtained by applying a gate voltage $V_g$ to the response electrode for a certain period of time.

Next, the second detection step is executed: a membrane potential of the target cells is changed, and a second pulse voltage V2 is applied to the response electrode 104 to generate a second electric field F2 between the response electrode 104 and the gate end 116 of the base 102, and the second detection current generated by the base 102 is measured.

In an embodiment, changing the membrane potential of the target cells includes, for instance, changing a resting potential (i.e., polarized potential) of the target cells to a depolarized potential. In another embodiment, changing the membrane potential of the target cells includes, for instance, changing a depolarized potential of the target cells to a polarized potential. A method of changing the membrane potential of the target cells includes, for instance, applying an external stimulus to the target cells. In an embodiment, the external stimulus includes, for instance, a change in ion concentration, a chemical signal molecule, a light, or a sound wave, but the invention is not limited thereto. In the present embodiment, the type and concentration of the ions are not particularly limited as long as the membrane potential of the target cells can be changed from a polarized potential to a depolarized potential or changed from a depolarized potential to a polarized potential. When the membrane potential of the target cells is changed, the local charge distribution of the base is also changed, such that the solution capacitance is changed. Therefore, current gain is changed.

In the present embodiment, the definitions of the second pulse voltage V2 and the second electric field F2 are the same as those of the first pulse voltage V1 and the first electric field F1.

In the present embodiment, the second detection step can include the following sub-steps: a third current gain generated by the base is measured and a fourth current gain generated by the base is measured, wherein the third current gain is a current gain before the test solution is placed, the fourth current gain is a current gain after the membrane potential of the target cells is changed, and the second detection current (i.e., change in current gain) is the fourth current gain minus the third current gain.

In the present embodiment, a sign of the first detection current and a sign of the second detection current are opposite. For instance, when the value of the first detection current is positive, the value of the second detection current is negative. Alternatively, when the value of the first detection current is negative, the value of the second detection current is positive. When the above conditions are met, the presence of the target cells can be confirmed. Specifically, when the membrane potential of the target cells is changed (changed from polarized potential to depolarized potential or changed from depolarized potential to polarized potential), the current gain is changed. Therefore, the sign of the detection current measured after the membrane potential of the target cells is changed and the sign of the detection current measured before the membrane potential of the target cells is changed are opposite, so as to ensure the presence of the target cells.

Moreover, in comparison to detecting membrane potential using a microelectrode or a patch clamp, the sensor device used in the method of detecting cells of the invention is non-invasive. Moreover, the membrane potential of cells can currently be measured using a potentiometric molecular probe. However, the issue of photo-bleaching readily occurs to the fluorescent probe. The sensor device used in the method of detecting cells of the invention can detect a change in the membrane potential of a single cell and a large number of calibration procedures is not needed.

In the following, the method of detecting cells and properties thereof provided by the invention are described in detail via experimental examples, but the following experimental examples are not intended to limit the invention.

EXAMPLE

In the present example, the sensor device 200 shown in FIG. 2 was used for detection, wherein the distance between the response electrode of the sensor device and the gate end: 65 μm; and the area of the detection region: 10×60 μm². Moreover, a specific aptamer of a human colorectal cancer cell line HCT-8 cell was bonded to the response electrode of the sensor device.

[Measurement Conditions of Sensor Device]

In the present embodiment, source and drain properties were measured and recorded using an Agilent B1530/B1500A semiconductor parameter analyzer. Operating conditions: $V_D$=2.5 V; $V_g$=2 V; pulse duration=50 μs. The change in source current before and after a gate bias is applied is defined as the current gain.

[Cell Lines and Reagents Used]

In the present embodiment, human colorectal cancer cell line HCT-8 cells were used as the target cells. The HCT-8 cells were cultured in an RPMI-1640 cell culture medium (Invitrogen Co., USA). During a subsequent electrical measurement, the HCT-8 cells were suspended in a Hank balanced salt solution having calcium ions and magnesium ions (hereinafter HBSS w/Ca&Mg), a Hank balanced salt solution without calcium ions and magnesium ions (hereinafter HBSS w/o Ca&Mg), or a Hank balanced salt solution having calcium ions (hereinafter HBSS w/Ca) to prepare a test solution. In the Hank balanced salt solution having calcium ions and magnesium ions (HBSS w/Ca&Mg), the calcium ions were 1.2 mM and the magnesium ions are 0.8 mM. The calcium ions in a Hank balanced salt solution having calcium ions (HBSS w/Ca) was 1.2 mM.

Experimental Example 1

[Sensor Device Response to Depolarization Induced by KCl]

In experimental example 1, HBSS w/Ca&Mg containing different KCl concentrations (5 mM, 10 mM, 20 mM, 30 mM) were used as reference solutions, and the reference solutions were used as baselines for the calculation of the sensor device. Specifically, HBSS w/Ca&Mg containing different KCl concentrations were respectively dripped on a response electrode, and measurement was performed via the same conditions above ($V_D$=2.5 V; $V_g$=2 V; pulse duration=50 μs) to obtain individual first current gains (I1, I2, I3, and I4). The first current gains formed the baselines.

Next, the HBSS w/Ca&Mg on the response electrode was washed away via an elution buffer. The HCT-8 cells were respectively suspended in HBSS w/Ca&Mg containing different KCl concentrations (5 mM, 10 mM, 20 mM, and 30 mM) to obtain test solutions.

Next, the test solutions were respectively dripped on a response electrode, and measurement was performed via the same conditions above ($V_D$=2.5 V; $V_g$=2 V; pulse duration=50 μs) to obtain individual second current gains (I1', I2', I3', and I4').

Lastly, the corresponding first current gains I were subtracted from the second current gains I' to obtain the individual detection currents (i.e., change in current gain (Δ current gain)).

Figure 3A:
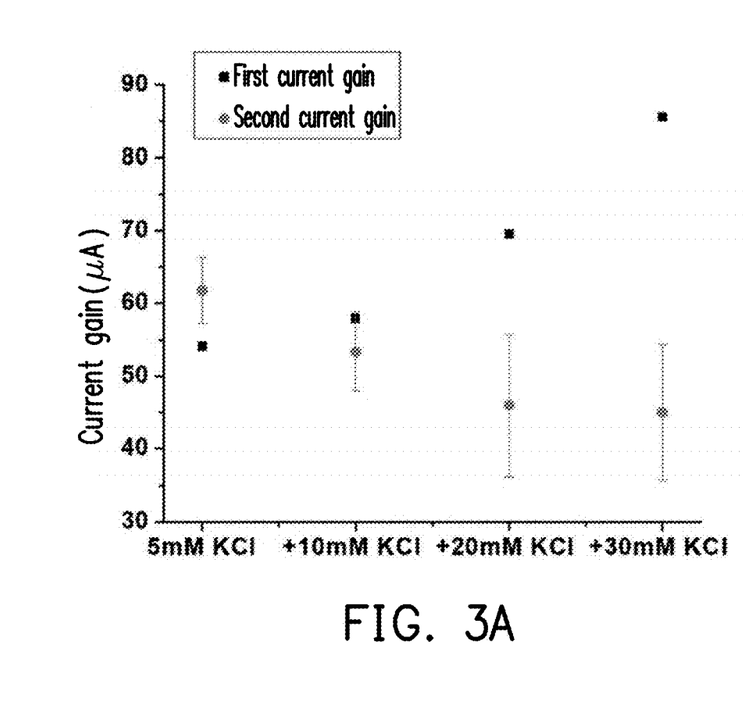
FIG. 3A shows the relationship between current gain and KCl concentration.
Figure 3B:
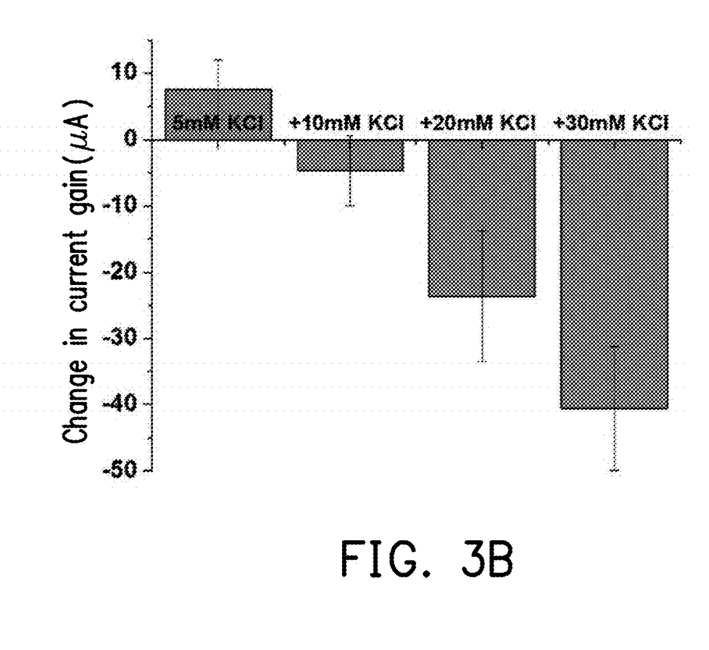
FIG. 3B shows the relationship between Δ current gain and KCl concentration.

FIG. 3A shows the relationship between current gain and KCl concentration. FIG. 3B shows the relationship between Δ current gain and KCl concentration.

In FIG. 3A, the individual first current gains (i.e., current gains obtained without the target cells) form the baselines. It can be seen from FIG. 3A that, the first current gain is increased as the KCl concentration in HBSS w/Ca&Mg is increased (5 mM to 30 mM). This is due to an increase in the total ion concentration in the reference solution, and therefore the solution capacitance is increased, such that current gain is increased. When the target cells are captured by an aptamer and the extracellular KCl concentration is increased, the measured second current gain is less than the corresponding baseline.

It can be seen from FIG. 3B that, the value of the detection current (i.e., the second current gain minus the first current gain) of the target cells measured at a KCl concentration of 5 mM is positive, and the value of the detection current (i.e., the second current gain minus the first current gain) of the target cells measured at a KCl concentration of 10 mM to 30 mM is negative. It can be known from the above content that, the target cells have a polarized potential at a KCl concentration of 5 mM. When the extracellular KCl concentration is increased, K ions outside the cell membrane flow into the cells such that the negative charge inside the cells is weakened, and the membrane potential of the cells is changed (i.e., depolarized) and current gain is changed. Therefore, the sign of the detection current measured after the membrane potential of the target cells is changed and the sign of the detection current measured before the membrane potential of the target cells is changed are opposite, and therefore the presence of the target cells can be ensured.

[Dynamic Sensor Device Response to Continuously Changing Divalent Cation Concentrations]

Experimental Example 2

In the present embodiment, HBSS w/o Ca&Mg and HBSS w/Ca&Mg containing different calcium ion concentrations (0.01 mM, 0.1 mM, 1 mM, and 1.2 mM) and magnesium ion concentrations (0.004 mM, 0.04 mM, 0.4 mM, and 0.8 mM) were used as reference solutions, and the reference solutions above were used as baselines for the calculation of the sensor device. Specifically, the reference solutions above were dripped on a response electrode, and measurement was performed via the same conditions above ($V_D$=2.5 V; $V_g$=2 V; pulse duration=50 μs) to obtain individual first current gains (I1, I2, I3, I4, and I5). The first current gains formed the baselines.

Next, the HBSS w/Ca&Mg on the response electrode was washed away via an elution buffer. The HCT-8 cells were suspended in HBSS w/o Ca&Mg to obtain a test solution.

Next, the test solution was dripped on a response electrode and the calcium ion concentration and the magnesium ion concentration in the HBSS w/Ca&Mg were gradually increased ($[Ca^{2+}]_o$: 0.01 mM, 0.1 mM, 1 mM, and 1.2 mM; $[Mg^{2+}]_o$: 0.004 mM, 0.04 mM, 0.4 mM, and 0.8 mM), and measurement was performed at each concentration point via the same conditions above ($V_D$=2.5 V; $V_g$=2 V; pulse duration=50 μs) to obtain individual second current gains (I1', I2', I3', I4', and I5').

Lastly, the corresponding first current gains I were subtracted from the second current gains I' to obtain the individual detection currents (i.e., change in current gain (Δ current gain)).

Figure 4A:
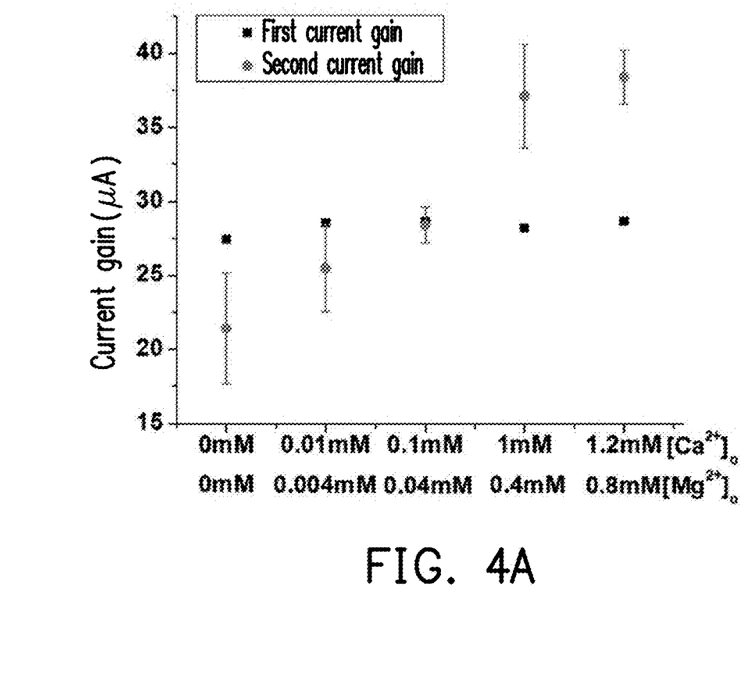
FIG. 4A shows the relationship between current gain and calcium ion and magnesium ion concentrations.
Figure 4B:
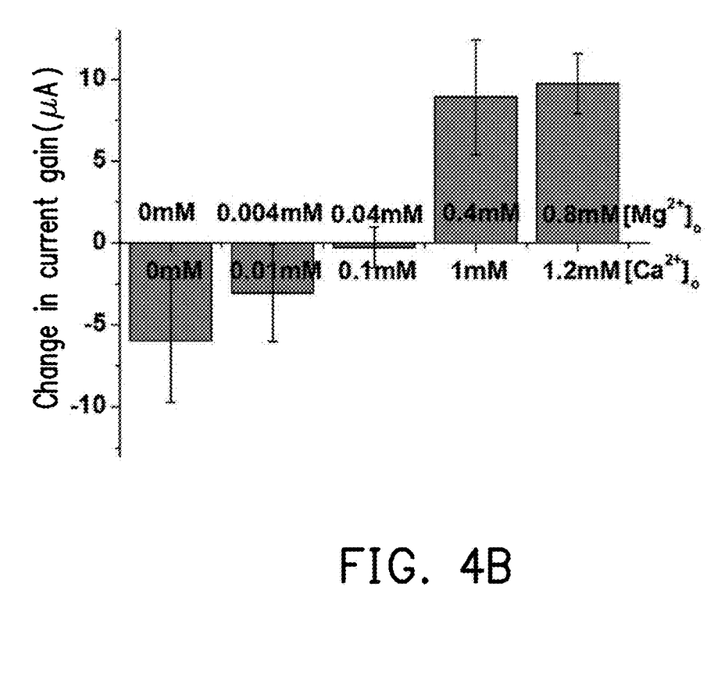
FIG. 4B shows the relationship between Δ current gain and calcium ion and magnesium ion concentrations.

FIG. 4A shows the relationship between current gain and calcium ion and magnesium ion concentrations. FIG. 4B shows the relationship between Δ current gain and calcium ion and magnesium ion concentrations.

It can be seen from FIG. 4A that, when the divalent cation concentration (i.e., calcium ions and magnesium ions) is increased, the baseline is not significantly changed. This is due to the negligible change in the overall ion concentration in the reference solution, and therefore the current gain of the sensor device remains stable. When the target cell suspension is in a Hank balanced salt solution without calcium ions and magnesium ions (HBSS w/o Ca&Mg) (i.e., the calcium ion and magnesium ion concentrations are 0), the target cells are captured on the sensor device, and the measured second current gain is less than the baseline. When the calcium ion and magnesium ion concentrations are gradually increased, the measured second current gain is continuously increased.

It can be seen from FIG. 4A and FIG. 4B that, when the value of the measured detection current (i.e., the second current gain minus the first current gain) of the target cells at a divalent cation concentration of 0 is negative, the target cells have a depolarized membrane potential. As the concentration of the divalent cation added is increased, the current gain is continuously increased. When the calcium ion and magnesium ion concentrations of the target cells are respectively 0.1 mM and 0.04 mM, the value of the measured detection current is positive, indicating the target cells are repolarized.

Experimental Example 3

[Cadmium Block of Calcium Channels]

Currently, the ion channels present on the cell membrane can be closed using channel blockers, and the cell membrane potential is changed as a result. The cadmium ion is a known calcium channel blocker, and a divalent cation can be used as a calcium antagonizer, and therefore extracellular magnesium ions ($Mg^{2+}$) can close the calcium channels and maintain the physiological concentration of intracellular calcium ions. The outer radii of calcium ions ($Ca^{2+}$) and cadmium ions ($Cd^{2+}$) are similar, and therefore cadmium ions can also block the calcium channels present on the cell membrane. $Cd^{2+}$ is a currently known permeant channel blocker sensitive to membrane potential change. In other words, $Cd^{2+}$ not only can close calcium ion channels, but can also enter cells and compete with $Ca^{2+}$ in the cytoplasm.

In experimental example 3, HBSS w/Ca and HBSS w/Ca containing different cadmium ion concentrations (5 uM, 10 uM, 20 uM, 50 uM, and 100 uM) are used as reference solutions, and the baselines of the sensor device were calculated using the reference solutions. Specifically, the reference solutions above were dripped on a response electrode, and measurement was performed via the same conditions above ($V_D$=2.5 V; $V_g$=2 V; pulse duration=50 μs) to obtain individual first current gains (I1, I2, I3, I4, I5, and I6). The first current gains formed the baselines.

Next, the HBSS w/Ca on the response electrode was washed away via an elution buffer. The HCT-8 cells were respectively suspended in HBSS w/Ca to obtain a test solution.

Next, the test solution was dripped on a response electrode and the cadmium ion concentration in HBSS w/Ca was gradually increased (5 uM, 10 uM, 20 uM, 50 uM, and 100 uM), and measurement was performed at each concentration point via the same conditions above ($V_D$=2.5 V; $V_g$=2 V; pulse duration=50 μs) to obtain individual second current gains (I1', I2', I3', I4', I5', and I6').

Lastly, the corresponding first current gains I were subtracted from the second current gains I' to obtain the individual detection currents (i.e., change in current gain (Δ current gain)).

Figure 5A:
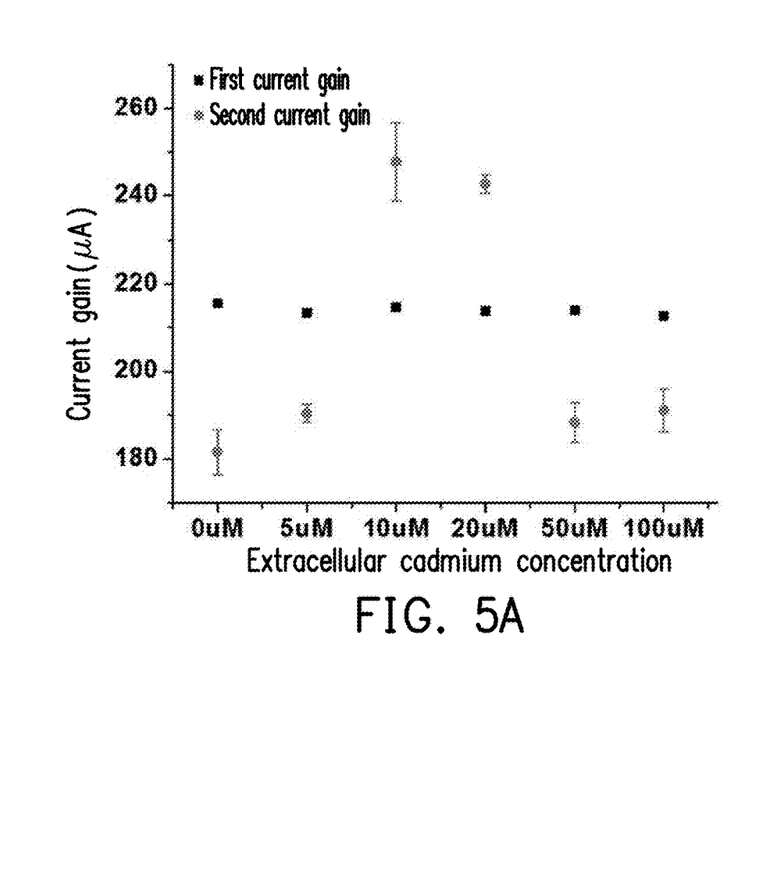
FIG. 5A shows the relationship between current gain and cadmium ion concentration.
Figure 5B:
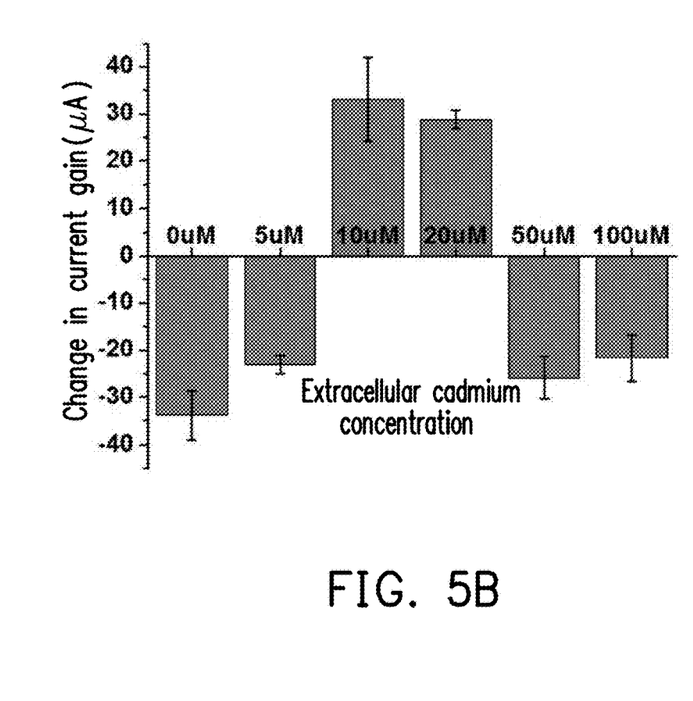
FIG. 5B shows the relationship between A current gain and cadmium ion concentration.

FIG. 5A shows the relationship between current gain and cadmium ion concentration. FIG. 5B shows the relationship between Δ current gain and cadmium ion concentration.

In FIG. 5A, the individual first current gains (i.e., current gains obtained without the target cells) form the baselines.

It can be seen from FIG. 5A and FIG. 5B that, when the target cells are suspended in HBSS w/Ca without cadmium ions (i.e., cadmium ion concentration is 0), the target cells are captured on the sensor device, the measured second current gain is less than the baseline, and the value of the detection current is a negative value. The results above show that the target cells have a depolarized membrane potential.

When the extracellular cadmium ion concentration in the solution is increased from 0 μM to 20 μM, the measured second current gain is increased, and the detection current obtained at the cadmium ion concentrations of 10 μM and 20 μM is a positive value. The reason is that the extracellular low-concentration $Cd^{2+}$ can block the calcium channels. Therefore, the target cells originally having depolarized membrane potential can be repolarized due to the closure of the calcium channels.

When the cadmium concentration is further increased from 20 μM to 100 μM, the measured second current gain is reduced, and the value of the detection current is a negative value. This phenomenon is due to the penetrating property of the cadmium ions into channel blockers, and therefore extracellular cadmium ions penetrate into the cells. Moreover, the cadmium ions penetrating into the cells increase the calcium ion concentration inside the cells such that the cells are depolarized.

Based on the above, in the method of detecting cells of the invention, by changing the membrane potential of the target cells to detect a change in the current gain in order to determine the presence of the target cells, the method has the properties of high sensitivity, high accuracy, and low detection limit.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A method of detecting cells, comprising:
    a preparation step in which a sensor device is provided, wherein the sensor device comprises a base and at least one response electrode, and the response electrode is spaced apart from the base with respect to a gate end of the base;
    a first detection step in which a test solution containing a target cell is placed on the response electrode, and a first pulse voltage is applied to the response electrode to generate a first electric field between the response electrode and the gate end of the base, and a first detection current generated by the base is measured; and a second detection step in which a membrane potential of the target cell is changed, and a second pulse voltage is applied to the response electrode to generate a second electric field between the response electrode and the gate end of the base, and a second detection current generated by the base is measured, wherein a sign of the first detection current and a sign of the second detection current are opposite, wherein the first detection step comprises: measuring a first current gain generated by the base and measuring a second current gain generated by the base, wherein the first current gain is a current gain before the test solution is placed, the second current gain is a current gain after the test solution is placed, and the first detection current is the second current gain minus the first current gain.

2. The method of detecting cells of claim 1, wherein the first electric field and the second electric field are F, and 0.1 V/cm≤F≤10 V/cm.

3. The method of detecting cells of claim 1, wherein the sensor device further comprises an acceptor disposed on a surface of the response electrode, and the acceptor can be specifically bonded to the target cell.

4. The method of detecting cells of claim 3, wherein the acceptor is an antibody or an aptamer.

5. The method of detecting cells of claim 1, wherein the second detection step comprises:

measuring a third current gain generated by the base and measuring a fourth current gain generated by the base, wherein the third current gain is a current gain before the test solution is placed, the fourth current gain is a current gain after the membrane potential of the target cell is changed, and the second detection current is the fourth current gain minus the third current gain.

6. The method of detecting cells of claim 1, wherein a method of changing the membrane potential of the target cell comprises applying an external stimulus to the target cell.

7. The method of detecting cells of claim 6, wherein the external stimulus comprises a change in an ion concentration, a chemical signal molecule, a light, or a sound wave.

8. The method of detecting cells of claim 1, wherein the first pulse voltage and the second pulse voltage are pulse voltages having an adjustable pulse width and height.

9. The method of detecting cells of claim 7, wherein the pulse width is not greater than $10^{-3}$ seconds.

10. The method of detecting cells of claim 1, wherein the response electrode and the gate end of the base are located on a same plane.

* * * * *